United States Patent [19]

Ohsumi et al.

[11] Patent Number: 5,679,845
[45] Date of Patent: Oct. 21, 1997

[54] PROCESS FOR PRODUCING TAURINE ANALOGUES

[75] Inventors: Tomoko Ohsumi; Manabu Katsumata, both of Kanagawa-ken; Tomoyasu Tashiro, Tokyo; Saburoh Uchikuga, Kanagawa-ken, all of Japan

[73] Assignee: Sogo Pharmaceutical Company Limited, Tokyo, Japan

[21] Appl. No.: 696,791

[22] Filed: Aug. 14, 1996

[51] Int. Cl.$^6$ .................................................. C07C 313/02
[52] U.S. Cl. .................................................. 562/126
[58] Field of Search ................................ 562/126, 29

[56] References Cited

U.S. PATENT DOCUMENTS 2,212,783  8/1940  Lavine .

FOREIGN PATENT DOCUMENTS 2223549  5/1990  Japan .

OTHER PUBLICATIONS

Chemical Abstracts, vol. 70, No. 9, 12 May 1969, Columbus, Ohio, Abstract no. 88237.
W. Mansfield Clark et al., "Biochemical Preparations", *Biochemical Preparations, Inc.*, 10(72–75, 1963.
CA 83:53205 J Med Chem (1975) 18(5) 502–5 "Probiotics etc" Fujii.
CA 78:15513—SU 350787 Sep. 13, 1972 Hypotaurine Pustoshkin.
CA 95:149880 J. Labelled Compd Radiopharm (1981) 18(5) 765–8 Fellman sythesis–etc.

*Primary Examiner*—José G. Dees
*Assistant Examiner*—Jean F. Vollano
*Attorney, Agent, or Firm*—Browdy and Neimark

[57] ABSTRACT

The present invention relates to a process for producing amino/guanidinothiosulfonic acid, which comprises treating a styrenedivinylbenzene copolymer sulfonate of amino/guanidinoethyl disulfoxide into contact with an alkali, selectively eluting amino/guanidinosulfinic acid, then reacting this product in a non-aqueous solvent in the presence of a base, and passing the reaction product through a weakly acidic cation exchange resin column; in accordance with the present invention, hypotaurine, thiotaurine and the like having a high purity can industrially be produced.

2 Claims, No Drawings

PROCESS FOR PRODUCING TAURINE ANALOGUES

DETAILED DESCRIPTION OF THE INVENTION

1. Field of the Invention

The present invention relates to processes for producing taurine analogues. More specifically, the present invention relates to industrial processes in which taurine analogues such as hypotaurine, thiotaurine and the like can be obtained in high yields.

2. Prior Art

Amino/guanidinosulfinic acid such as hypotaurine or the like is present as a vital substance and plays an important role. A sulfinic acid group in the molecule of this compound is reductive, and this compound exhibits special amphoteric properties because it has an amino group, a guanidino group and a sulfinic acid group. Since this compound is a vital substance, it exhibits a low toxicity, and is therefore expected as medications, toiletries, functional food or food additives. Amino/guanidinosulfonic acid such as thiotaurine or the like is also useful as medications, toiletries, food and drink.

Among these taurine analogues, hypotaurine which is an example of amino/guanidinosulfinic acid is produced, for example, according to the usual method described in Biochemical Preparations 10, p. 72 (1963), by oxidizing cysteamine hydrochloride (1) with hydrogen peroxide in the presence of potassium iodide as a catalyst to form cystamine disulfoxide dihydrochloride (2), adding sodium hydroxide to this compound (2) to conduct alkali decomposition in an aqueous solution, thereby forming hypotaurine (s), cystamine (4) and sodium chloride (5), applying them to a strongly acidic cation exchange resin column [Rp(SO₃H)n] to adsorb all of these compounds to the cation exchange resin (6, 7, 8), and eluting only hypotaurine (3) with aqueous ammonia as schematically shown below.

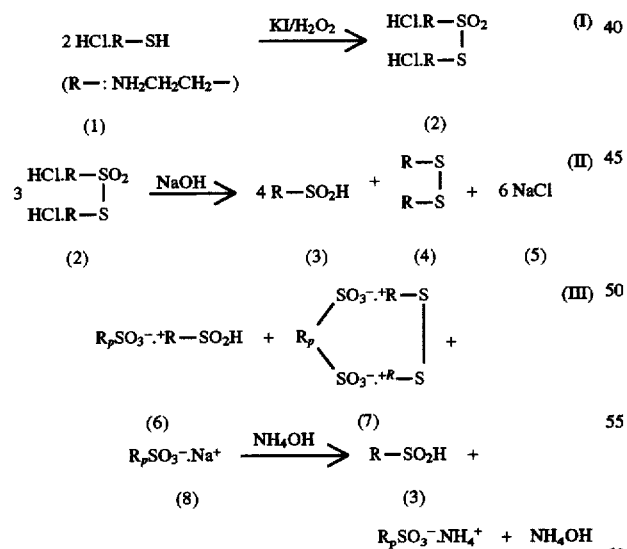

Since hypotaurine (3) formed through the reaction represented by formula (II) in the above-mentioned reaction scheme is an amphoteric substance and has a sulfinic acid (—SO₂H) group similar to sulfonic acid (—SO₃H), it is hardly adsorbed to a sulfonic acid-type strongly acidic cation exchange resin. If this substance is completely adsorbed thereto, a huge amount of the sulfonic acid-type strongly acidic cation exchange resin is required. Besides, the strongly acidic cation exchange resin is also required to remove an alkali to be added. This method is not suitable for an industrial production.

Among these taurine analogues, thiotaurine which is an example of amino/guanidinothiosulfonic acid is produced according to the usual method described in Biochemical Preparations 10, p. 72 (1963), by using the following composition

| | |
|---|---|
| hypotaurine (sulfinic acid) | 220 parts |
| 0.2 N sodium hydroxide | 1 part |
| sulfur | 70 parts |
| alcohol | 20 parts |
| yield | 75% | and especially using a sodium hydroxide aqueous solution in order to dissolve hypotaurine and sulfur. After the completion of the reaction, the reaction mixture is allowed to stand overnight, and crystals are collected by decantation, and washed with carbon disulfide and alcohol to obtain thiotaurine. However, in this reaction system, the side reaction is liable to occur. Consequently, the yield and qualities are lowered.

Problems To Be Solved by the Invention

The present invention aims to solve these problems and to develop novel processes for producing taurine analogues at high efficiency.

Means Taken For Solving the Problems

In order to solve the above-mentioned problems associated with the conventional methods and achieve the above-mentioned object, the present inventors have assiduously conducted study. Consequently, it has been found that:

(1) cystamine disulfoxide dihydrochloride (2) is strongly adsorbed to a strongly acidic cation exchange resin, and insoluble styrenedivinylbenzene sulfonate of cystamine disulfoxide is formed at high efficiency, and therefore a quite small amount of a strongly acid cation exchange resin is sufficient, and (2) when this salt is brought into contact with an alkali, the reactions (II) and (III) proceed simultaneously, and hypotaurine is formed and eluted at good efficiency, and a high-quality product is obtained.

These findings have led to the development of an industrially excellent process in which a high-quality product can be produced in high yield stably and economically.

That is, a process has been found in which cystamine disulfoxide dihydrochloride (2) is directly passed through a strongly acidic cation exchange resin to form novel styrenedivinylbenzene sulfonate (9) without conducting alkali decomposition of cystamine disulfoxide as in the conventional method, then this compound (9) is subjected to alkali decomposition in the column to form hypotaurine (3) and hypotaurine (3) formed is eluted alone. In this process, hypotaurine can be economically produced in high yield and high purity using quite a small amount of the strongly acidic cation exchange resin as compared with the conventional method.

The reaction scheme is shown below.

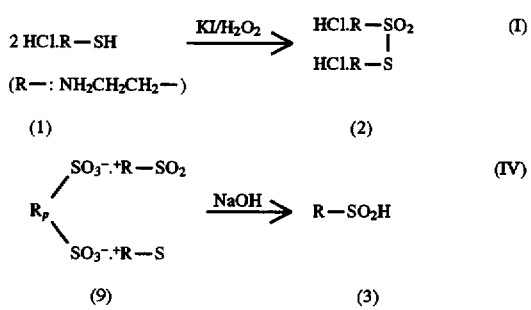

The present invention has been achieved on the basis of these new findings and further studies. One of the basic technological concepts in the present invention is a process in which a styrenedivinylbenzene copolymer sulfonate of amino/guanidinoethyl disulfoxide represented by formula (A)

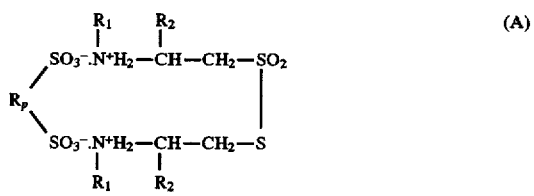

wherein
$R_p$ represents a styrenedivinylbenzene copolymer,
$R_1$ represents H or —C(NH)NH$_2$, and
$R_2$ represents H or —COOH,
is treated with an alkali to produce amino/guanidinosulfinic acid represented by formula (B)

wherein $R_1$ and $R_2$ are as defined above.

More particularly, the compound of formula (A) is brought into contact with an alkali, and decomposed to selectively elute sulfinic acid of formula (B).

According to the process of the present invention, a lot of excellent effects are brought forth as compared with the conventional method which will be described in detail by referring to the following Comparative Examples.

COMPARATIVE EXAMPLE 1

Comparison with respect to an amount of a resin required:

The conventional method and the process of the present invention were compared with respect to an amount of hypotaurine eluted which was measured using a strongly acidic cation exchange resin (Diaion SK1B, made by Mitsubishi Kagaku K. K.) as an ion exchange resin. The results are shown in Table 1.

TABLE 1

| Conventional method | | | | |
|---|---|---|---|---|
| Amount of a cation exchange resin/Theoretical (times): | 1 | 2 | 3 | 4 |
| Amount of hypotaurine leaked (%): | 49.9 | 19.9 | 8.8 | 1.4 |
| Process of the present invention | | | | |

TABLE 1-continued

| | | | | |
|---|---|---|---|---|
| Amount of a cation exchange resin/Theoretical (times): | 1.0 | 1.1 | 1.2 | 1.3 |
| Amount of hypotaurine leaked (%): | 6.3 | 5.5 | 1.0 | 0.9 |

On the basis of the above-mentioned results, the conventional method was compared with the process of the present invention in regard to the amount of the resin required when the amount of hypotaurine leaked was 1.4%. The result is as follows.

Ratio of the conventional method to the process of the present invention=4.0 times to 1.17 times=3.42

This indicates that the amount of the resin required in the conventional method is at least 3.42 times that of the resin required in the process of the present invention. Since the resin [Rp(SO$_3$H)$_n$] for RpSO$_3^-$.Na$^+$ of formula (III) is not required in the process of the present invention, this ratio is actually still higher. In other words, a heavy load can be put on the resin device in the process of the present invention, and the cost for equipment investment can advantageously be reduced.

Further, in the process of the present invention, the reaction solution can be directly brought into contact with the resin without isolating cystamine disulfoxide obtained by the reaction (I) to form styrenedivinylbenzene sulfonate (9). Accordingly, it is possible to simplify the process, to shorten the production period and to reduce the labor cost. Thus, the process of the present invention is quite economical.

COMPARATIVE EXAMPLE 2

Comparison with respect to the improvement of the yield:

The conventional method was compared with the process of the present invention in regard to the yield of hypotaurine to cystamine disulfoxide. The results are shown in Table 2. As is clear from these results, the yield was much improved in the process of the present invention as compared with the conventional method. In other words, the process of the present invention can reduce the production cost and improve the productivity.

TABLE 2

| Hypotaurine yield (%) on cystamine disulfoxide | |
|---|---|
| Conventional method: | 50 |
| Process of the present invention: | 83 |

COMPARATIVE EXAMPLE 3

Comparison with respect to the improvement of qualities:

Hypotaurines which were produced by the conventional method and the process of the present invention were compared with respect to the appearance, the purity and the content of taurine which is an oxidized product of hypotaurine. The results are shown in Table 3. As is clear from these results, the present invention can more improve the purity and the value of the product.

TABLE 3

|                              | Appearance   | Purity (%) | Taurine content (%) |
|------------------------------|--------------|------------|---------------------|
| Conventional method          | light yellow | 98.0       | 1.5                 |
| Process of the present invention | white    | 99.5       | trace               |

In the present invention, a strongly acidic cation exchange resin having styrenedivinylbenzenesulfonic acid which forms a salt with cystamine disulfoxide is commercially available.

As the alkali which is used to decompose styrenedivinylbenzene sulfonate of cystamine disulfoxide and elute hypotaurine, inorganic and organic bases are available. Alkali metal hydroxide and ammonia are preferable.

If hypotaurine analogues having a carboxylic acid and/or a guanidino group instead of the amino group in the molecule are subjected to the above-mentioned procedure, the same effects are attainable.

The present inventors have developed the above-mentioned efficient process for producing the compound of formula (B) such as hypotaurine or the like, and have conducted further study in order to develop a new efficient process for producing thiotaurine by improving the defects associated with the conventional method. Consequently, they have found that when hypotaurine is reacted under a condition which is closer to an anhydrous condition, thiotaurine can be obtained in high yield.

The present invention has been achieved on the basis of these new findings and further study. One of the basic technological concepts in the present invention is a process in which amino/guanidinosulfinic acid represented by formula (B)

wherein $R_1$ represents H or $-C(NH)NH_2$, and $R_2$ represents H or $-COOH$, is brought into contact with a weakly acidic cation exchange resin in the presence of a base under an anhydrous condition to produce amino/guanidinothiosulfonic acid represented by formula (C)

wherein $R_1$ and $R_2$ are as defined above.

More particularly, the compound of formula (B) is reacted with sulfur in suspension in an anhydrous solvent and in the presence of a base, and the reaction mixture is then passed through a weakly acidic cation exchange resin to produce thiosulfonic acid of formula (C).

In the present invention, the reaction in the anhydrous condition means that hypotaurine and sulfur are reacted in suspension, and that the reaction product, thiotaurine is also obtained in suspension state.

The base to be used may be an inorganic or organic base. Preferable examples of the base include alkali metal, alkali metal hydroxide, alkali metal alcoholate, (bi)carbonate of ammonia and lower alkyl N-substituted substance. Specific examples thereof include metallic sodium, sodium hydroxide, potassium hydroxide, sodium methylate, potassium ethylate, ammonium (bi)carbonate, trimethylamine, diethylamine and monomethylamine and so on.

The solvent which is used in the present invention is preferably an anhydrous solvent. As the anhydrous solvent, a solvent which is generally used in organic syntheses is available. The anhydrous solvent is preferably a lower alkanol. Specific examples of the lower alkanol include methyl alcohol, ethyl alcohol and isopropyl alcohol and so on.

The reaction is appropriately conducted under reflux at a boiling point of the solvent for from 0.5 to 3 hours.

In the process of the present invention, sulfinic acid of formula (B) is used as a starting material. Commercially available sulfinic acid and sulfinic acid produced from the compound of formula (A) by the above-mentioned method can be used.

The present invention can attain a lot of excellent effects compared with the conventional method, which will be described in detail by referring to the following Comparative Examples.

COMPARATIVE EXAMPLE 4

The components in the above-mentioned composition of the reaction mixture except that 1 part of a 0.2N sodium hydroxide aqueous solution was replaced with 4.6 parts of metallic sodium were reacted in suspension for 3 hours. Then, the reaction mixture was subjected to the same treatment as in the conventional method to obtain thiotaurine. The process of the present invention was compared with the conventional method with respect to the yield of thiotaurine. The results are shown in Table 4.

TABLE 4

|           | Conventional method | Process of the present invention |
|-----------|---------------------|----------------------------------|
| Yield (%): | 75                 | 82.5                             |

It was found that when the reaction mixture in suspension was dissolved in water and passed through a weakly acidic cation exchange resin column, the yield was further improved and high-purity thiotaurine was obtained.

Thus, the reaction mixture in suspension obtained by the reaction in the non-aqueous system is dissolved in water at 40° C., and passed through the weakly acidic cation exchange resin column, and the eluate is concentrated, whereby high-quality thiotaurine can be obtained in high yield.

COMPARATIVE EXAMPLE 5

Sodium methylate (14.8 g), 70.8 g of a sulfur powder and 1,300 ml of methanol were added to 218 g (2.0 mols) of hypotaurine. The mixture was refluxed at 65° C. for 3 hours, and methanol was distilled away under reduced pressure until the amount of it became small. Water (1,600 ml) was added thereto, and the mixture was dissolved by heating. Excess sulfur was removed using 10 g of activated carbon as a filtration aid.

The filtrate was passed through 300 ml of a Diaion WK-10 (made by Mitsubishi Kagaku K. K.), and eluate was concentrated. Twenty grams of activated carbon was added thereto, and the filtrate was further concentrated. By addition of 1,000 ml of methanol and cooling the mixture sufficiently, crystals were completely precipitated. The resulting crystals were separated by filtration, and dried to obtain 258.4 g of white crystals (yield: 91.4%).

The process of the present invention was compared with the conventional method with respect to qualities and yield.

The results are shown in Table 5. From this Table 5, it is clear that the process of the present invention is superior to the conventional method.

TABLE 5

|  | Conventional method | Process of the present invention |
|---|---|---|
| Yield (%) | 75 | 91.4 |
| Properties |  |  |
| Appearance | light yellow | white |
| Clarity of solution | slightly turbid | clear |
| Purity | 97.0% | 99.8% |
| pH | 5.0 to 6.0 (not fixed) | 5.0 |

Thiotaurine has been described above. The thiotaurine analogues having the carboxylic acid and/or the guanidino group instead of the amino group in the molecule [compounds of formula (C)] can be produced by the above-mentioned procedure, and the above-mentioned effects are attainable.

The present invention is illustrated more specifically by referring to the following Examples.

EXAMPLE 1

Production of hypotaurine

A solution of 114 g (1.0 mol) of cysteamine hydrochloride and 1.0 g of potassium iodide in 200 ml of water was charged in a 2-liter reaction vessel, and a solution prepared by diluting 1.5 mols of 30% hydrogen peroxide with 150 ml of water was added dropwise thereto while being cooled with ice. The mixture was stirred overnight at room temperature, and then concentrated under reduced pressure. The precipitated crystals were filtered, and dried to obtain 116 g of cystamine disulfoxide dihydrochloride (yield: 90%).

Cystamine disulfoxide dihydrochloride (25.7 g, 0.1 mols) was dissolved in water. The solution was passed through 150 ml of a Diaion SK1B column, and then washed with water. Sodium hydroxide (12 g) was dissolved in 200 ml of water, and the solution was passed through the resin column. Subsequently, 20 g of 25% ammonia was diluted with 200 ml of water. The ammonia solution was passed through the resin column, and washed with water. The eluate from the Diaion SK1B column was passed through 150 ml of a Diaion WK-10 column, and concentrated under reduced pressure. Crystals were precipitated to obtain 11.9 g of hypotaurine (yield: 82.1%).

EXAMPLE 2

Production of cysteinesulfinic acid

Cystine (4.8 g, 0.2 mols) was mixed with 900 ml of formic acid and 400 ml of conc. hydrochloric acid, and 50 ml of a 30% hydrogen peroxide solution was added thereto dropwise in the range of from 20° to 23° C. The reaction was conducted in the range of from 20° to 23° C. The reaction mixture was stirred overnight at room temperature, and then concentrated. When the reaction mixture became a syrup, an appropriate amount of a 25% aqueous ammonia was added thereto to adjust the pH to 3. The precipitated crystals were dispersed in methanol, filtered, and dried to obtain 36.0 g of cystine disulfoxide.

This cystine disulfoxide (13.6 g, 0.05 mols) was dissolved in 250 ml of formic acid. The solution was passed through 150 ml of a Diaion SK1B column, and washed with 300 ml of water. A solution of 11.4 g of sodium hydroxide in 200 ml of water was passed through this resin column, and then washed with 150 ml of water. Subsequently, a solution of 17.5 g of a 25% aqueous ammonia in 200 ml of water was passed through the resin column, and then washed with water. This eluate was passed through 150 ml of a Diaion WK-10 column. The resulting eluate was concentrated, crystallized, filtered and dried to obtain 8.7 g of cysteine-sulfinic acid (yield: 85%).

EXAMPLE 3

Production of hypotaurocyamine

2-Aminoethylisothiuronium dihydrochloride (38.2 g, 0.2 mols) and 8.0 g of sodium hydroxide were dissolved in 200 ml of water, and a solution prepared by diluting 0.1 mols of a 30% hydrogen peroxide solution with 20 ml of water was added dropwise thereto at 30° C. or less. The mixture was stirred overnight at room temperature, 35% hydrochloric acid (10.5 g) was diluted with 20 ml of water, and the solution was added to the mixture to adjust the pH to 1. Potassium iodide (0.2 g) was added thereto, 45.3 g of a 30% hydrogen peroxide solution was diluted with 80 ml of water, and the solution was added dropwise to the mixture. This reaction mixture was stirred overnight at room temperature.

This reaction mixture was passed through 158 ml of a Diaion SK1B column, and washed with 300 ml of water. A solution of 12 g of sodium hydroxide in 200 ml of water was passed through this resin column, and then washed with 150 ml of water. Subsequently, 20.5 g of 25% aqueous ammonia was diluted with 200 ml of water. The solution was passed through the resin column, and then washed with water. This eluate was passed through 300 ml of a Diaion WK-10, concentrated, and crystallized by methanol to obtain 14.7 g of hypotaurocyamine (yield: 73%).

EXAMPLE 4

Production of N-amidinocysteinesulfinic acid

Example 2 was repeated except that cystine disulfoxide was replaced with 17.8 g (0.05 mols) of N-amidinocystine disulfoxide. As a result, 10.8 of N-amidinocysteinesulfinic acid were obtained (yield: 82.5%).

EXAMPLE 5

Production of thiotaurine

Hypotaurine (109 g, 1.0 mol), 5.2 g of sodium hydroxide and 35.3 g of a sulfur powder were suspended in 650 ml of methanol, refluxed for 3 hours, and the solvent was distilled away under reduced pressure until the amount of it became small. Eight-hundred milliliters of water was added thereto, and the mixture was dissolved by heating at 42° C. Excess sulfur was removed using 5 g of activated carbon as a filtration aid.

The filtrate was passed through 300 ml of a Diaion WK-10 column, and the eluate was concentrated under reduced pressure until small amounts of crystals were precipitated. The pressure was returned to normal, and the crystals were dissolved at 42° C. Activated carbon (12.5 g) was added thereto. The mixture was stirred at 42° C. for 30 minutes, decolorized and filtered. The filtrate was concentrated under reduced pressure. The crystals were completely precipitated with 500 ml of methanol, allowed to stand overnight in a freezer, and filtered. The crystals were washed well with methanol, and then vacuum-dried to obtain 128.2 g of thiotaurine white crystals (yield: 90.9%).

The resulting crystals exhibited the following physicochemical properties, and it was identified that the crystals were thiotaurine.

TLC (eluent: water-saturated phenol): 1 spot

IR: Characteristic absorption was observed around 3140 $cm^{-1}$, 1600 $cm^{-1}$, 1470 $cm^{-1}$, 1185 $cm^{-1}$, 1045 $cm^{-1}$ and 715 $cm^{-1}$.

Elemental analysis:
Theoretical: C:H:N=17.0:5.0:9.9
Found: C:H:N=16.8:4.9:9.9
Melting point: 208.4° C.
pH: 5.04

EXAMPLE 6

Production of thiotaurine

Hypotaurine (32.7 g, 0.3 mols), 0.9 g of metallic sodium and 10.6 g of a sulfur powder were suspended in 550 ml of methanol, and refluxed for 3 hours. Subsequently, the methanol was distilled away under reduced pressure until the amount of it became small. Eight-hundred milliliters of water was added thereto, and the mixture was dissolved by heating at 42° C. Excess sulfur was removed using 5 g of activated carbon as a filtration aid.

The filtrate was passed through 100 ml of a Diaion WK-10 column, and the eluate was concentrated under reduced pressure until small amounts of crystals were precipitated. The pressure was returned to normal, and the crystals were dissolved at 42° C. Activated carbon (10 g) was added thereto. The mixture was stirred at 42° C. for 30 minutes, decolorized and filtered. The filtrate was concentrated under reduced pressure. The crystals were completely precipitated with 500 ml of methanol, allowed to stand overnight in a freezer, and filtered. The crystals were washed well with methanol, and then vacuum-dried to obtain 38.6 g of thiotaurine white crystals (yield: 91.2%).

The resulting crystals exhibited the following physicochemical properties, and it was identified that the crystals were thiotaurine.

TLC (eluent: water-saturated phenol): 1 spot

IR: Characteristic absorption was observed around 3140 $cm^{-1}$, 1600 $cm^{-1}$, 1470 $cm^{-1}$, 1185 $cm^{-1}$, 1045 $cm^{-1}$ and 715 $cm^{-1}$.

Elemental analysis:
Theoretical: C:H:N=17.0:5.0:9.9
Found: C:H:N=16.9:4.9:9.9
Melting point: 208.9° C.
pH: 5.05

EXAMPLE 7

Production of thiotaurine

Hypotaurine (109 g, 1.0 mol), 13.5 g of triethylamine and 35.3 g of a sulfur powder were suspended in 650 ml of methanol, and refluxed for 3 hours. Subsequently, the solvents were distilled away under reduced pressure until the amount of them became small. Eight-hundred milliliters of water was added thereto, and the mixture was dissolved by heating at 42° C. Excess sulfur was removed using 5 g of activated carbon as a filtration aid.

The filtrate was passed through 300 ml of a Diaion WK-10 column, and the eluate was concentrated under reduced pressure until small amounts of crystals were precipitated. The pressure was returned to normal, and the crystals were dissolved at 42° C. Activated carbon (12.5 g) was added thereto. The mixture was stirred at 42° C. for 30 minutes, decolorized and filtered. The filtrate was concentrated under reduced pressure. The crystals were completely precipitated with 500 ml of methanol, allowed to stand overnight in a freezer, and filtered. The crystals were washed well with methanol, and then vacuum-dried to obtain 132.0 g of thiotaurine white crystals (yield: 93.7%).

The resulting crystals exhibited the following physicochemical properties, and it was identified that the crystals were thiotaurine.

TLC (eluent: water-saturated phenol): 1 spot

IR: Characteristic absorption was observed around 3140 $cm^{-1}$, 1600 $cm^{-1}$, 1470 $cm^{-1}$, 1185 $cm^{-1}$, 1045 $cm^{-1}$ and 715 $cm^{-1}$.

Elemental analysis:
Theoretical: C:H:N=17.0:5.0:9.9
Found: C:H:N=16.8:4.9:9.8
Melting point: 208.3° C.
pH: 5.07

EXAMPLE 8

Production of thiotaurocyamine

Hypotaurocyamine (151.2 g, 1.0 mol), 7.4 g of sodium methylate and 35.3 g of a sulfur powder were suspended in 650 ml of methanol, and refluxed for 3 hours. Subsequently, the methanol was distilled away under reduced pressure until the amount of it became small. Eight-hundred milliliters of water was added thereto, and the mixture was dissolved by heating at 42° C. Excess sulfur was removed using 5 g of activated carbon as a filtration aid.

The filtrate was passed through 300 ml of a Diaion WK-10 column, and the eluate was concentrated under reduced pressure until small amounts of crystals were precipitated. The pressure was returned to normal, and the crystals were dissolved at 42° C. Activated carbon (12.5 g) was added thereto. The mixture was stirred at 42° C. for 30 minutes, decolorized and filtered. The filtrate was concentrated under reduced pressure. The crystals were completely precipitated with 500 ml of methanol, allowed to stand overnight in a freezer, and filtered. The crystals were washed well with methanol, and then vacuum-dried to obtain 165.5 g of thiotaurocyamine white crystals (yield: 90.3%).

The resulting crystals exhibited the following physicochemical properties, and it was identified that the crystals were thiotaurine.

TLC (eluent: water-saturated phenol): 1 spot

Elemental analysis:
Theoretical: C:H:N=19.7:5.0:22.9
Found: C:H:N=19.6:4.8:22.9

EXAMPLE 9

Production of guanidinocysteinethiosulfonic acid

Guanidinocysteinesulfinic acid (195.2 g, 1.0 mol), 5.2 g of sodium hydroxide and 35.3 g of a sulfur powder were suspended in 650 ml of methanol, and refluxed for 3 hours. Subsequently, the methanol was distilled away under reduced pressure until the amount of it became small. Eight-hundred milliliters of water was added thereto, and the mixture was dissolved by heating at 42° C. Excess sulfur was removed using 5 g of activated carbon as a filtration aid.

The filtrate was passed through 300 ml of a Diaion WK-10 column, and the eluate was concentrated under reduced pressure until small amounts of crystals were precipitated. The pressure was returned to normal, and the crystals were dissolved at 42° C. Activated carbon (10 g) was added thereto. The mixture was stirred at 42° C. for 30 minutes, decolorized and filtered. The filtrate was concentrated under reduced pressure. The crystals were completely precipitated with 500 ml of methanol, allowed to stand overnight in a freezer, and filtered. The crystals were washed well with methanol, and then vacuum-dried to obtain 208.0 g of guanidinocysteinethiosulfonic acid white crystals (yield: 91.5%).

The resulting crystals exhibited the following physico-chemical properties, and it was identified that the crystals were guanidinocysteinethiosulfonic acid.

Clarity of solution: clear
Purity: 99.7%
TLC (eluent: water-saturated phenol): 1 spot
Elemental analysis:
Theoretical: C:H:N=21.4:4.0:18.5
Found: C:H:N=21.0:3.9:18.4

EXAMPLE 10

Production of cysteinethiosulfonic acid

Cysteinesulfinic acid (153.2 g, 1.0 mol), 13.5 g of triethylamine and 35.3 g of a sulfur powder were suspended in 650 ml of methanol, and refluxed for 3 hours. Subsequently, the solvents were distilled away under reduced pressure until the amount of them became small. Eight-hundred milliliters of water was added thereto, and the mixture was dissolved by heating at 42° C. Excess sulfur was removed using 5 g of activated carbon as a filtration aid.

The filtrate was passed through 300 ml of a Diaion WK-10 column, and the eluate was concentrated under reduced pressure until small amounts of crystals were precipitated. The pressure was returned to normal, and the crystals were dissolved at 42° C. Activated carbon (12.5 g) was added thereto. The mixture was stirred at 42° C. for 30 minutes, decolorized and filtered. The filtrate was concentrated under reduced pressure. The crystals were completely precipitated with 500 ml of methanol, allowed to stand overnight in a freezer, and filtered. The crystals were washed well with methanol, and then vacuum-dried to obtain 168.6 g of cysteinethiosulfonic acid white crystals (yield: 91.0%).

The resulting crystals exhibited the following physico-chemical properties, and it was identified that the crystals were cysteinethiosulfonic acid.

Clarity of solution: clear
Purity: 99.8%
TLC (eluent: water-saturated phenol): 1 spot
Elemental analysis:
Theoretical: C:H:N=19.5:3.8:7.6
Found: C:H:N=19.3:3.7:7.7

Effects of the Invention

In accordance with the present invention, a product having high quality and purity can be produced in high yield industrially at good efficiency.

What we claim is:

1. A process for producing amino/guanidinosulfinic acid represented by formula (B)

$$R_1NH-\underset{\underset{R_2}{|}}{CH}-CH_2-SO_2H \qquad (B)$$

wherein $R_1$ represents H or $-C(NH)NH_2$, and
$R_2$ represents H or $-COOH$, which comprises bringing a styrenedivinylbenzene copolymer sulfonate of amino/guanidinoethyl disulfoxide represented by formula (A)

$$R_p\underset{\diagdown}{\overset{\diagup}{}}\begin{matrix}SO_3^-.N^+H_2-\underset{\underset{R_2}{|}}{\overset{\overset{R_1}{|}}{CH}}-CH_2-SO_2\\ \\ SO_3^-.N^+H_2-\underset{\underset{R_2}{|}}{\overset{\overset{R_1}{|}}{CH}}-CH_2-S\end{matrix}\Big| \qquad (A)$$

wherein $R_p$ represents a styrenedivinylbenzene copolymer, and
$R_1$ and $R_2$ are as defined above,
into contact with an alkali, decomposing said salt, and selectively eluting amino/guanidinosulfinic acid.

2. The process of claim 1, wherein amino/guanidinosulfinic acid of formula (B) is one member selected from the group consisting of hypotaurine, cysteinesulfinic acid, hypotaurocyamine and N-amidinocysteinesulfinic acid.

* * * * *